United States Patent [19]

Vandermeerssche

[11] Patent Number: 4,507,953
[45] Date of Patent: Apr. 2, 1985

[54] ABRASION TESTING MACHINE

[76] Inventor: Gaston A. Vandermeerssche, 9240 N. Sleepy Hollow La., Milwaukee, Wis. 53217

[21] Appl. No.: 411,673

[22] Filed: Aug. 26, 1982

[51] Int. Cl.³ .............................................. G01N 3/56
[52] U.S. Cl. ......................................... 73/7; 73/667; 73/432 SD
[58] Field of Search .............. 73/7, 667, 432 SD, 778, 73/818, 819, 825, 821

[56] References Cited

U.S. PATENT DOCUMENTS

| | | |
|---|---|---|
| 991,381 | 5/1911 | Simmers . |
| 1,635,787 | 7/1927 | Hort . |
| 2,305,783 | 12/1942 | Heymann et al. . |
| 2,348,189 | 5/1944 | Buchanan et al. . |
| 2,438,755 | 3/1948 | Larsen . |
| 2,438,756 | 3/1948 | Larsen . |
| 2,466,807 | 4/1949 | Hein . |
| 2,512,304 | 6/1950 | Calver . |
| 2,677,960 | 5/1954 | Moses ...................................... 73/67 |
| 2,725,745 | 12/1955 | Hubbard et al. . |
| 3,037,378 | 6/1962 | Hill . |
| 3,049,913 | 8/1962 | Hunt . |
| 3,176,505 | 4/1965 | Hendrickson . |
| 3,187,566 | 6/1965 | Coombs . |
| 3,241,358 | 3/1966 | Booth et al. . |
| 3,277,697 | 10/1966 | Wittkuhns . |
| 3,282,088 | 11/1966 | Joannou . |
| 3,985,026 | 10/1976 | Griffin et al. ........................ 73/150 |
| 4,130,007 | 12/1978 | Hayashi .................................... 73/7 |

FOREIGN PATENT DOCUMENTS

| | | |
|---|---|---|
| 1980986 | 12/1967 | Fed. Rep. of Germany . |
| 1573854 | 5/1970 | Fed. Rep. of Germany . |

OTHER PUBLICATIONS

"Closed Loop", MTS Systems Corporation, vol. 11, No. 1, p. 9.

*Primary Examiner*—Charles Frankfort
*Assistant Examiner*—Denis E. Corr
*Attorney, Agent, or Firm*—Quarles & Brady

[57] ABSTRACT

An abrasion testing machine has a vibrating horizontal platform which supports a six pack of test specimens, such as beverage cans. Hydraulic cylinder controlled pressure plates are applied to the sides of the array of test specimens and to the top of the array as the specimens are vibrated. The amount of pressure is controllable by a control cylinder for each of the pressure cylinders and the speed and magnitude of vibration is adjustable by controlling motor speed and the position of an adjustable linkage between the motor and the platform.

16 Claims, 4 Drawing Figures

ABRASION TESTING MACHINE

BACKGROUND OF THE INVENTION

This invention relates to testing equipment, and more particularly to a machine for testing the abrasion resistance of coatings.

Aluminum and steel beverage cans are provided with coatings, including such items as inks and varnishes, which both protect the surface and provide labeling. The beverage cans are shipped by a variety of modes of transportation, most typically by rail and truck. The cans are exposed to vibrations of all types during shipment and the vibrations can be very detrimental to both the coatings on the cans and the base stock of the cans. The cans are typically packed in six pack carriers and stacked next to each other and on top of each other. The surfaces of adjacent cans in contact will rub against each other as a result of the motions. Serious problems can result from such motions. Not only will the costings themselves be rubbed off, but the base stock of the cans can be abraded to the point where holes are formed in the cans.

Very large, complex equipment has been used in the past to simulate, in a laboratory environment, conditions of transportation so as to test the abrasion resistance of various coatings on beverage cans. The test results are predictive of what will occur in actual transportation conditions. In addition to being bulky, such equipment is relatively expensive. As a result such equipment has in the past been found in only a few central testing locations and it has been necessary to send cans to such locations for testing.

By my invention I provide a small, compact testing machine which can provide test results equivalent to that of the large, expensive equipment now in use and which, because of its small size and relatively low cost, can be installed at the can makers plant sites or at the coating manufacturers plant sites. The testing equipment can also be used for the testing of the abrasion resistance of coatings generally, and not only those which are used in beverage cans.

SUMMARY OF THE INVENTION

In accordance with my invention I provide a testing machine which includes a platform adapted to support a test specimen, means for applying side-wise forces against the test specimen on such platform, means for applying a downward force on the top of the test specimen, and means for vibrating the platform and downward force applying means relative to each other.

In a preferred form of the embodiment the test specimen is an array of cans in the form of a six pack. The platform is vibrated while the top of the cans are held stationary. The amplitude and frequency of the vibration and the magnitude of the side-wise and vertical forces are all adjustable. The platform together with the force applying means are housed totally within a cabinet such that the environment within such cabinet can be controlled both as to temperature and humidity.

It is a principal object of the present invention to provide a compact testing machine for the vibration testing of the abrasion resistance of coatings.

It is another object of the invention to provide such a machine which can simulate the results of the vibrations encountered during transportation of stacked and packed cylindrical, coated objects such as cans.

The foregoing and other objects and advantages of the invention will appear in the following detailed description of the preferred embodiment. In such description, reference is made to the accompanying drawings which illustrate a preferred embodiment of the invention.

DETAILED DESCRIPTION OF THE PREFERRED EMBODIMENT

Figure 1:
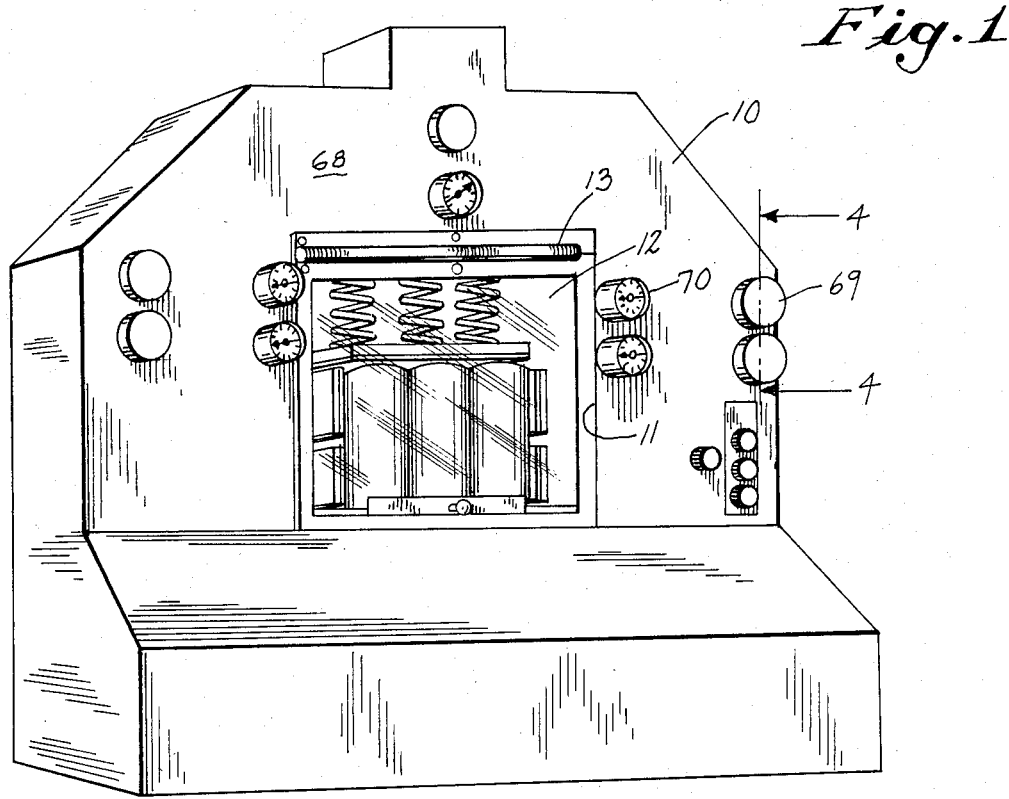
FIG. 1 is a view in perspective of a testing machine in accordance with the present invention.
Figure 4:
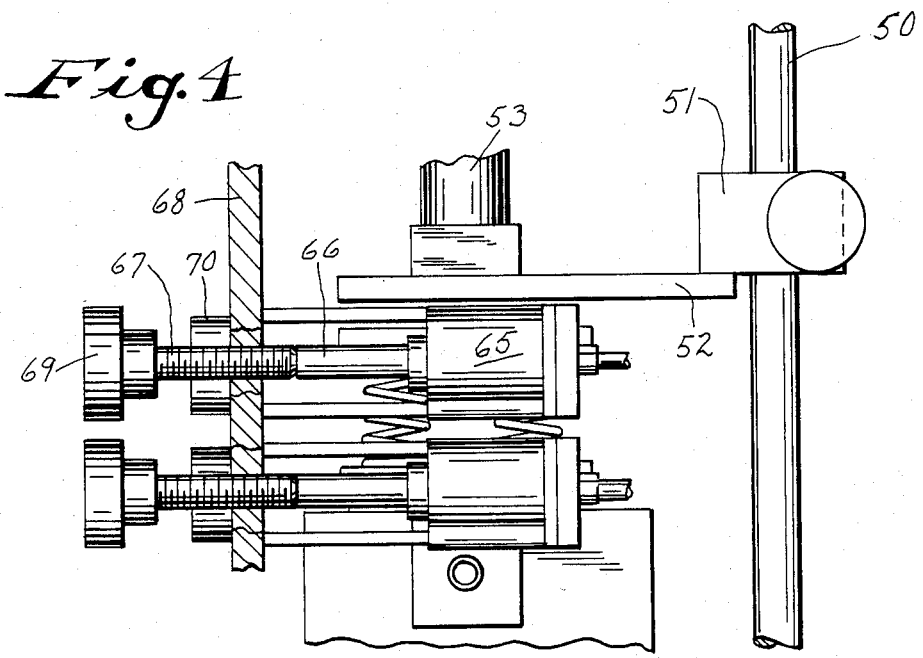
FIG. 4 is a side view in elevation of a portion of the mechanism of FIG. 2 and taken from the plane of the line 4—4 of FIG. 1.

Referring now to the drawings, a testing machine in accordance with this invention includes an outer housing or cabinet 10 having a doorway 11 in its front face which is closed by a clear plastic door 12 mounted at its top edge on a piano hinge 13. Inside the housing 10 is a horizontal vibratory platform 15 which is mounted by a series of four bearing blocks 16 on a pair of spaced horizontal rods 17 which are in turn mounted at their ends on pedestals 18 which rise from a floor 19. The platform 15 is free to move in a horizontal direction along the parallel shafts 17 and is moved in that direction in a controlled manner by an adjustable speed d.c. electric motor 20 whose output shaft 21 mounts an eccentric plate 22. The eccentric plate 22 has a series of threaded mounting openings 23 which receive threaded screws to attach a block 24 to the face of the eccentric plate 22. A lever arm 25 is journaled at one end on a stub shaft 26 extending from the block 24. The opposite end of the lever arm 25 is provided with a longitudinal slot 27 which receives a threaded bolt 28 that extends into an opening in a bracket 29 depending from the horizontal platform 15.

An upright mounting plate 31 is attached to each end of the platform 15. The mounting plates support identical left and right horizontal force applying assemblies. Only the left assembly, as viewed in FIGS. 2 and 3, will be described. The horizontal force applying assembly includes upper and lower hydraulic cylinders 32 and 33, respectively, which are attached to the mounting plate 31. The piston rods 34 and 35 of the cylinders 32 and 33, respectively, extend through openings in the mounting plate 31 and are connected to respective upper and lower plates 36 and 37 each of which mount one end of a pair of compression springs 38. The other end of the compression springs 38 are mounted in upper and lower pressure plates 39 and 40, respectively. Each of the pressure plates 39 and 40 has a rubber or other elastomer surface 41.

A rear plate 45 is attached to the rear of the platform 15 between the mounting plates 31. A backup plate 46 is mounted on the front face of the rear plate 45 and is either formed of or has a coating of Teflon.

A pair of upright standards 50 rise from the floor 19 behind the platform 15. The standards mount a pair of releasable clevises 51 which in turn mount and support a mounting plate 52. The mounting plate 52 mounts a hydraulic cylinder 53 whose piston rod 54 projects through an opening in the mounting plate 52. An intermediate plate 55 is secured to the piston rod 54 below the mounting plate 52 and six compression springs 56 are mounted on the underside of the intermediate plate 55. The springs 56 in turn mount a top pressure plate 57. The top pressure plate 57 has a bottom surface 58 formed of rubber or other elastomer.

As illustrated in the drawings, the testing machine is particularly adapted for testing the abrasion resistance of coatings on beverage cans which are typically arrayed in a six pack configuration. The array of cans is mounted in the testing equipment through the doorway 11 on a tray 59 which has an upper surface of rubber or other elastomer. The array of cans is positioned against the backup plate 46. The pressure plates 39 and 40 of the left and right pressure assemblies as well as the upper pressure plate 57 can be brought to bear on the array of cans.

Figure 2:
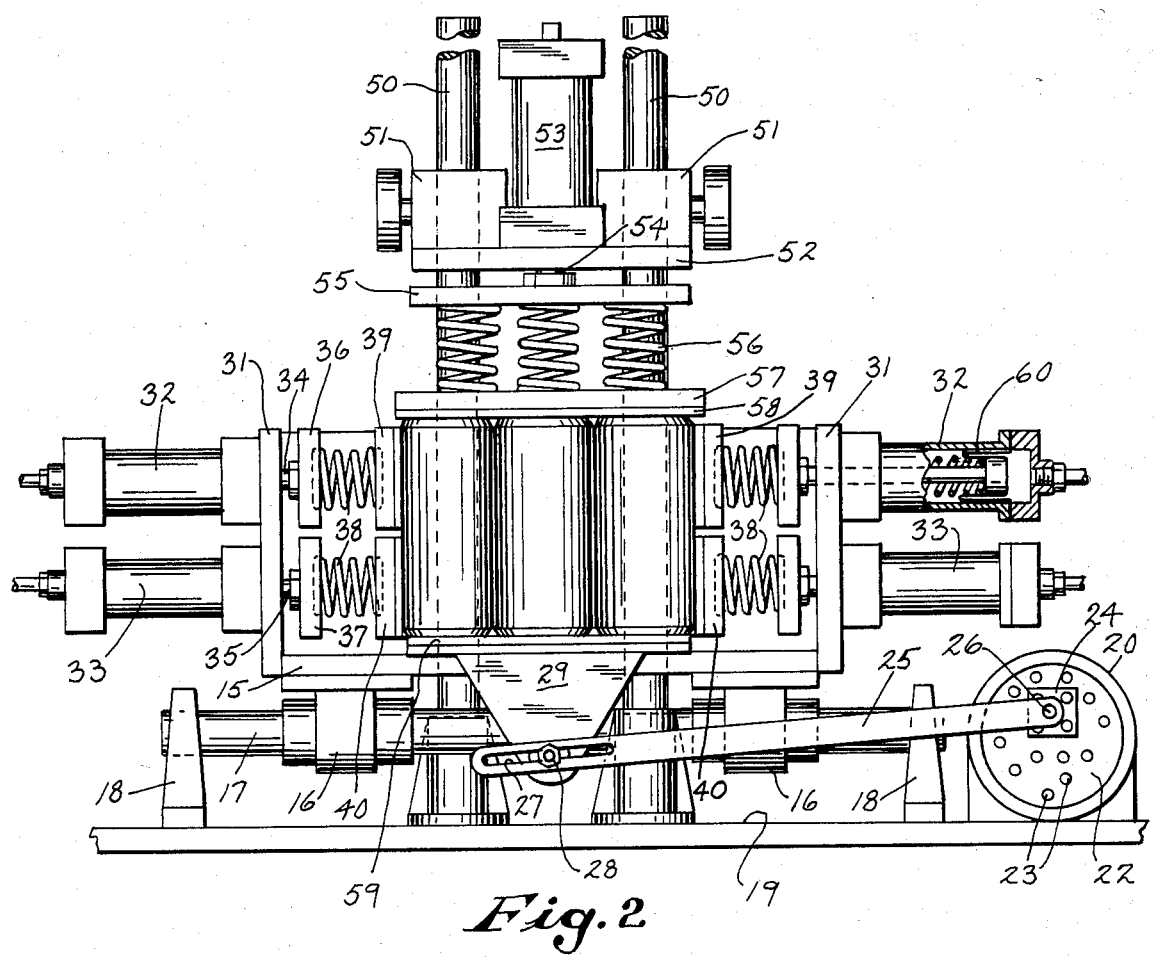
FIG. 2 is a view in vertical elevation of the testing apparatus with the cabinet removed, and illustrating the vibrating platform as well as the mechanism for applying forces on the test specimens.
Figure 3:
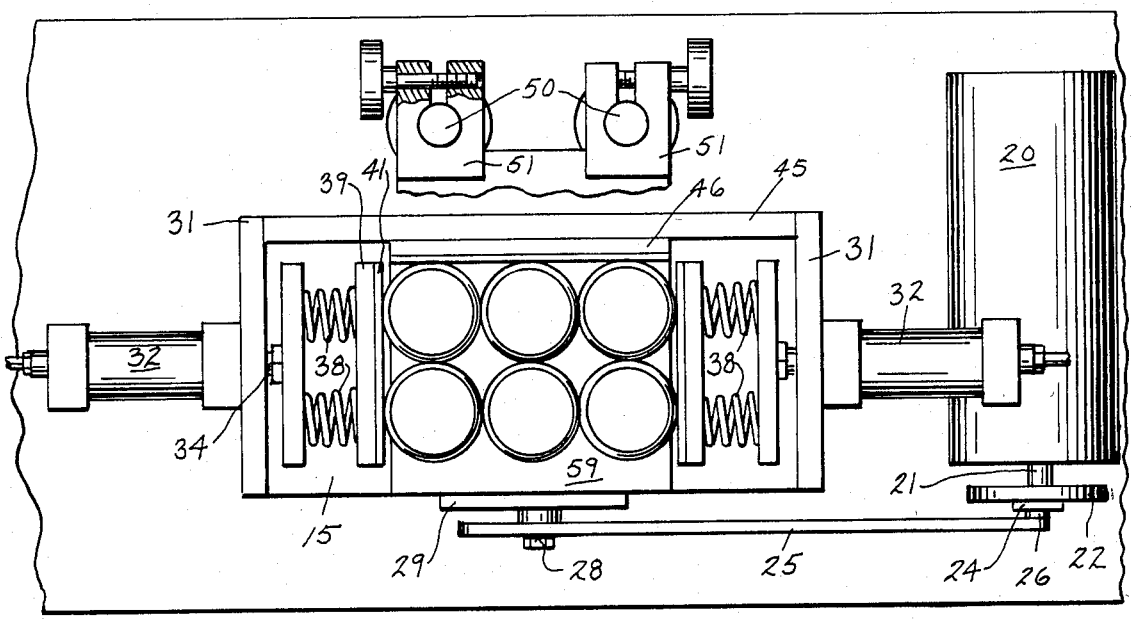
FIG. 3 is a top view of the mechanisms of FIG. 2 with the vertical force applying mechanism partially broken away for clarity of illustration.

The pressures exerted the cans by the upper and lower pressure plates 39 and 40 of the left and right assemblies and by the top pressure plate 57 are all adjustable. As shown in FIG. 2, each of the cylinders 32, 33 and 53 has a rolling diaphragm 60 which separates the cylinder head end from the rod end of the cylinder. The pistons are spring biased to a position retracted within the cylinders. Pressure applied on the head end will cause the rod to extend outwardly of the cylinder and exert increasing pressure on the cans through the springs 56 and 38 and the pressure plates 39, 40 and 57.

The amount of hydraulic fluid pressure exerted on the head ends is controlled by a separate control cylinder for each of the cylinders 32, 33 and 53. The control cylinder 65 is typical. The control cylinders are identical to the slave cylinders 32, 33 and 53 in that they include a rolling diaphragm formed over the end of the piston. However, the rod 66 of the control cylinder 65 is connected to a threaded shaft 67 which is received in a threaded opening in the front face 68 of the housing 10. A knob 69 is mounted on the threaded shaft 67 outside of the housing 10. Rotation of such knobs will adjust the axial position of the piston rod within each of the control cylinders thereby adjusting the position of the piston head within the cylinder. The head ends of each control cylinder and its slave cylinder are in fluid connection with each other so that the hydraulic fluid will be transferred between the hydraulic cylinders. The connection between the head ends of the control and slave cylinders are also connected to pressure gauges mounted on the front face of the housing 10, of which gauge 70 is typical. To increase the pressure exerted by any one of the pressure plates 39, 40 or 57, simply requires rotating a knob for that particular cylinder to extend the piston rod of the control cylinder further into its respective cylinder.

In operation, a six pack of cans or other test specimens are placed on the tray 59 and inserted through the open doorway 11. At this time, the left and right pressure plate assemblies would have been moved outwardly by rotation of the appropriate knobs to retract the piston rods of each of the slave cylinders 32 and 33 into its respective cylinder. The top pressure plate 57 is similarly moved out of the way. The entire top pressure plate assembly can be moved along the standards 50 to a proper position to accommodate cans or other test specimens of different heights. The test specimens are placed against the backup plate 46 and the side and top pressure plates 39, 40 and 57 are brought to bear on the array of cans or other test specimens. The entire platform 15 is then vibrated. The top force applying assembly including the top pressure plate 57 is mounted independent of the platform 15 so that it is stationary relative to the platform 15. As a result, the tops of the cans are held relatively stationary while the platform 15 vibrates and this action simulates the motion encountered during transportation.

During testing, the pressure applied by each of the separate pressure plates can be varied by adjustment through the respective knob, with the respective pressure gauges continuously providing a visual readout of the pressure being applied. Also, the speed of the motor 20 can be adjusted to vary the cycle of vibration. The cans or other test specimens will rub against each other as the platform is vibrated and the pressure applied by the various pressure plates will simulate the stacking and packaging of adjacent cans or other test specimens about the six pack.

The separate upper and lower side-wise pressure plates 39 and 40 can be used to simulate the effects of the typical plastic six pack carrier which engages the upper edges of the cans and which normally holds the upper edges together to a greater degree than the bottom edges of the cans.

The cans to be tested can be filled or unfilled and can have a base stock of metal or other materials such as fiberboard. Instead of the common six pack arrangement, a four-pack can also be tested. In fact, only two test specimens are needed to test the abrasion resistance of the coatings or base stock.

Although the invention has been described in terms of testing the abrasion coatings on cans, it can be used to test the coatings on any base stock. To do that it is only necessary to use test specimens which simulate the shape of cans. Such test specimens may be provided with holders on their outer surfaces in which strips of a coated base stock are mounted. The strips on adjacent test specimens are mounted so that they will rub against each other during vibration. Again, only two test specimens would be necessary.

The entire housing 10 can be enclosed and the environment within the housing controlled as to temperature and humidity to simulate different conditions encountered in the transportation of beverage cans and to determine the effect of such environmental differences upon the abrasion resistance of the can coatings. Very high humidity conditions can be simulated by enclosing the bottom of the test specimens in a plastic film filled with water.

In the preferred embodiment, the tops of the test specimens are held stationary relative to the vibrating platform. The machine could, however, employ a stationary platform and vibrate the top force applying means to achieve the necessary simulation of motions. Also, the platform and top force applying means could both be vibrated, but in opposition to each other, without departing from my invention.

I claim:

1. A testing apparatus, comprising:
   a horizontal platform adapted to support a test specimen;
   horizontal force applying means adapted to engage the sides of the test specimen and simultaneously apply continuous pressure to at least two said sides;

vertical force applying means adapted to engage the top of the test specimen and apply pressure thereto; and means for vibrating one of said platform and vertical force applying means relative to the other.

2. A testing apparatus in accordance with claim 1 wherein said horizontal and vertical force applying means are adjustable to vary the pressure applied against said test specimen.

3. A testing apparatus for at least two test specimens, comprising:

a horizontal platform adapted to support the test specimens;

means for vibrating said platform in a horizontal plane;

horizontal force applying means adapted to engage the sides of the test specimens and simultaneously apply continuous pressure to at least two said sides; and vertical force applying means adapted to engage the top of the test specimens and apply pressure thereto.

4. A testing apparatus in accordance with claim 3 wherein said horizontal and vertical force applying means are adjustable to vary the pressure applied against said test specimens.

5. A testing apparatus in accordance with claim 3 wherein said horizontal force applying means includes two sets of upper and lower pressure plates disposed on opposite sides of said platform, and means for mounting said sets of pressure plates to said platform.

6. A testing apparatus in accordance with claim 5 wherein said mounting means comprises:

upper and lower hydraulic cylinders for each set of pressure plates, said cylinders being supported by said platform; and a piston in each cylinder having its rod supporting one end of a compression spring, the other end of each compression spring mounting a respective one of said pressure plates.

7. A testing apparatus in accordance with claim 6 together with means for adjusting the head end pressure within each cylinder to thereby vary the pressure applied by each pressure plate.

8. A testing apparatus in accordance with claim 3 wherein said vertical force applying means includes a top pressure plate disposed above the test specimens, a vertical support disposed behind said platform, and means for mounting said top pressure plate on said vertical support.

9. A testing apparatus in accordance with claim 8 wherein said mounting means comprises a mounting plate adjustably secured to said support, a hydraulic cylinder secured to said mounting plate and having its piston rod mounting one end of a compression spring, the other end of the compression spring mounting said top pressure plate.

10. A testing apparatus in accordance with claim 9 together with means for adjusting the head end pressure within said cylinder to thereby vary the pressure applied by said top pressure plate.

11. A testing apparatus in accordance with claim 7 or 10 wherein said head end pressure adjusting means for each hydraulic cylinder comprises a control cylinder having its head end in fluid connection with the head end of said hydraulic cylinder and means for adjusting the position of the piston rod of said control cylinder to vary the pressure on the head end thereof.

12. A testing apparatus in accordance with claim 11 together with a pressure gauge in fluid communication with the head end of each hydraulic cylinder.

13. A testing apparatus in accordance with claim 3 wherein said vibrating means includes a lever arm connected at one end to said platform, a motor having an output shaft, and means mounting the other end of said lever arm eccentric to said output shaft.

14. A testing apparatus in accordance with claim 13 wherein said one end of said lever arm is adjustably connected to said platform and said other end of said lever arm is adjustably mounted on an eccentric plate supported on said motor shaft.

15. A testing apparatus in accordance with claim 13 wherein said motor is an adjustable speed electric motor.

16. A testing apparatus for identical test specimens which will rub against each other when vibrated, comprising:

a horizontal platform adapted to support the test specimens;

a housing surrouding the platform and including a door providing access to the platform;

means in said housing for vibrating said platform;

horizontal force applying means in said housing adapted to engage the sides of the test specimens and simultaneously apply continuous pressure to at least two said sides; and vertical force applying means adapted to engage the top of the test specimens and apply pressure thereto, said vertical force applying means being stationary relative to said vibrating platform.

* * * * *